United States Patent
Fisher

(10) Patent No.: US 6,708,689 B2
(45) Date of Patent: *Mar. 23, 2004

(54) ELIMINATION OF VAPOR ANAESTHETICS FROM PATIENTS AFTER SURGICAL PROCEDURES

(76) Inventor: Joseph A. Fisher, 113 Franmore Circle, Thornhill, ON (CA), L4J 3B9

(*) Notice: Subject to any disclaimer, the term of this patent is extended or adjusted under 35 U.S.C. 154(b) by 20 days.

This patent is subject to a terminal disclaimer.

(21) Appl. No.: 10/050,392

(22) Filed: Jan. 16, 2002

(65) Prior Publication Data

US 2003/0047187 A1 Mar. 13, 2003

Related U.S. Application Data

(63) Continuation of application No. 09/380,705, filed on Sep. 8, 1999, now Pat. No. 6,354,292, which is a continuation of application No. PCT/CA97/00186, filed on Mar. 19, 1999.

(51) Int. Cl.[7] ............................................... A61M 15/00
(52) U.S. Cl. ............................. 128/203.12; 128/204.23
(58) Field of Search .......... 128/204.18, 204.21–204.23, 128/204.26, 204.28, 204.29, 205.11, 205.13–205.17, 205.24, 200.22, 200.24, 203.12, 203.13, 203.28, 205.18, 910

(56) References Cited

U.S. PATENT DOCUMENTS

| | | | |
|---|---|---|---|
| 3,901,230 A | | 8/1975 | Henkin |
| 3,921,628 A | * | 11/1975 | Smythe et al. ......... 128/204.21 |
| 4,188,946 A | | 2/1980 | Watson et al. |
| 4,991,576 A | | 2/1991 | Henkin et al. |
| 5,320,093 A | | 6/1994 | Raemer |
| 5,398,675 A | | 3/1995 | Henkin et al. |
| 5,507,280 A | | 4/1996 | Henkin et al. |
| 5,509,406 A | * | 4/1996 | Kock et al. ............. 128/203.14 |
| 5,662,099 A | * | 9/1997 | Tobia et al. ............ 128/205.15 |
| 5,678,540 A | * | 10/1997 | Kock et al. ............. 128/205.13 |
| 5,857,458 A | * | 1/1999 | Tham et al. ............ 128/203.28 |
| 5,957,128 A | | 9/1999 | Hecker et al. |
| 6,125,848 A | * | 10/2000 | Hendrickson et al. . 128/204.22 |
| 6,131,571 A | * | 10/2000 | Lampotang et al. ... 128/204.21 |
| 6,152,131 A | * | 11/2000 | Heinonen ............... 128/204.23 |
| 6,216,690 B1 | * | 4/2001 | Keitel et al. ............ 128/203.12 |
| 6,295,985 B1 | * | 10/2001 | Kock et al. ............. 128/203.12 |
| 6,354,292 B1 | | 3/2002 | Fisher |

FOREIGN PATENT DOCUMENTS

WO     WO 96/36385     11/1996

* cited by examiner

Primary Examiner—Aaron J. Lewis
Assistant Examiner—Teena K Mitchell
(74) Attorney, Agent, or Firm—Stetina Brunda Garred & Brucker

(57) ABSTRACT

A breathing circuit system for ventilating an anaesthetized patient. The system comprises a standard primary circle anaesthetic circuit which itself comprises a one-way inspiratory limb for delivering re-breathed gas and a one-way expiratory limb for accepting expired gas. The breathing circuit system also includes a supplementary respiratory circuit which solely supplies non-rebreathed gas and comprises a source of non-rebreathed, substantially carbon dioxide-free gas, a non-rebreathed fresh gas reservoir for storing fresh gas, a source of non-rebreathed reserve gas containing carbon dioxide, and a gas delivery conduit. Disposed in communication with the inspiratory limb is a non-re-breathing valve, while disposed in communication with both the inspiratory limb and the delivery conduit is a three-way respiratory valve for selectively permitting passage of gas from the inspiratory limb or from the delivery conduit.

1 Claim, 12 Drawing Sheets

ELIMINATION OF VAPOR ANAESTHETICS FROM PATIENTS AFTER SURGICAL PROCEDURES

CROSS-REFERENCE TO RELATED APPLICATIONS

THIS APPLICATION IS A CONTINUATION OF Ser. No. 09/380,705 FILED Sep. 8, 1999 now U.S. Pat. No. 6,354,292, which is a continuation of PCT/CA97/00186 filed Mar. 19, 1999.

STATEMENT RE: FEDERALLY SPONSORED RESEARCH/DEVELOPMENT (Not Applicable)

FIELD OF THE INVENTION

The purpose of this invention is to provide a simple breathing circuit that can, for example, be added to a standard circle anaesthetic circuit known to persons skilled in the art to hasten recovery of patients administered vapour anaesthetics prior to an operation.

This invention also relates to the use of the breathing circuit in hastening the recovery of patients who have been administered vapour anaesthetics prior to surgical operation.

This invention also relates to methods of treatment of patients to hasten their recovery from administration of the vapour anaesthetics to them prior to surgical procedures.

BACKGROUND OF THE INVENTION

Physiology

Venous blood returns to the heart from the muscles and organs depleted of oxygen ($O_2$) and full of carbon dioxide ($CO_2$). Blood from various parts of the body is mixed in the heart (mixed venous blood) and pumped to the lungs. In the lungs the blood vessels break up into a net of small vessels surrounding tiny lung sacs (alveoli). The net of vessels surrounding the alveoli provides a large surface area for the exchange of gases by diffusion along their concentration gradients. A concentration gradient exists between the partial pressure of $CO_2$ ($PCO_2$) in the mixed venous blood ($PvCO_2$) and the alveolar $PCO_2$. The $CO_2$ diffuses into the alveoli from the mixed venous blood from the beginning of inspiration until an equilibrium is reached between the $PvCO_2$ and the alveolar $PCO_2$ at some time during the breath. When the subject exhales, the end of his exhalation is considered to have come from the alveoli and reflect the equilibrium concentration between the capillaries and the alveoli; the $PCO_2$ in this gas is called end-tidal $PCO_2$ ($P_{ET}CO_2$).

When the blood passes the alveoli and is pumped by the heart to the arteries it is known as the arterial $PCO_2$ ($PaCO_2$). The arterial blood has a $PCO_2$ equal to the $PCO_2$ at equilibrium between the capillaries and alveoli. With each breath some $CO_2$ is eliminated and fresh air containing little $CO_2$ (assumed to be O) is inhaled and dilutes the residual alveolar $PCO_2$, establishing a new gradient for $CO_2$ to diffuse out of the mixed venous blood into the alveoli. The rate of breathing, or ventilation (V), usually expressed in L/min, is exactly that required to eliminate the $CO_2$ brought to the lungs and maintain an equilibrium $PCO_2$ (and $PaCO_2$) of approximately 40 mmHg (in normal humans). When one produces more $CO_2$ (e.g. as a result of fever or exercise), more $CO_2$ is produced and carried to the lungs. One then has to breathe harder (hyperventilate) to wash out the extra $CO_2$ from the alveoli, and thus maintain the same equilibrium $PaCO_2$. But if the $CO_2$ production stays normal, and one hyperventilates, then the $PaCO_2$ falls.

It is important to note that not all V contributes to blowing off $CO_2$. Some V goes to the air passages (trachea and bronchi) and alveoli with little blood perfusing them, and thus doesn't contribute to blowing off $CO_2$. That the portion of V that goes well perfused alveoli and paticipates in gas exchange is called the alveolar ventilation (VA).

There are a number of circumstances in therapeutic medicine and research where we want the subject to breath harder but not to exchange his $PaCO_2$ (see Table 1).

TABLE I

| Type of Investigation | Reference | Method of adjustment | Source of $CO_2$ |
|---|---|---|---|
| Respiratory muscle fatigue | 5 | M | R |
|  | 12 | M | E |
|  | 7 | M | R |
| Respiratory muscle training | 2 | M | R |
|  | 3 | M | R |
| Increased V during anaesthesia | 6 | M | R |
| Carotid chemoreceptor function | 8 | M | E |
|  | 1 | M | E |
| Effect of hypoxia on symphathetic response | 10 | M | E |
|  | 4 | M | E |
| Control of respiration | 9 | A | E |
| Tracheobronchial tone | 11 | M | E |

1. Angell-James, J.E., Clarke, J.A., de Burgh Daly, M. and Taton, A., Carotid chemoreceptor function and structure in the atherosclerotic rabbit: respiratory and cardiovascular responses to hyperoxia and hypercapnia. Cardiovascular Research 23(6): 541-53, 1989.
2. Belman, M.J. and C. Mittman. Ventilatory muscle training improves exercise capacity in chronic obstructive pulmonary disease patients. Am. Rev. Respir. Dis. 121:273–280, 1980.
3. Bradley, M.E. and Leith, D.E. Ventilatory muscle training and the oxygen cost of sustained hyperpnea. J. Appl. Physiol. 45(6) 885–892, 1978.
4. Busija, D.W., Orr, J.A., Rankin, J.G.H., Liang, H.K. and Wagerle, L.C., Cerebral blood flow during normocapnic hyperoxia in the unanaesthetized pony. J. Apple. Physiol. 48(1):10–15, 1980.
5. Jonsson, L.O. Predictable $PaCO_2$ with two different flow settings using the Mapleson D. System. Acta Anaesthesiol Scand. 34:237–240, 1990.
6. McKerrow, C.B., and Otis, A.B. Oxygen cost of hyperventilation. J. Apple. Physiol. 9:375–79, 1956.
7. Robbins, P.A., Swanson, G.D. and Howson, M.G. A prediction-correction scheme for forcing alveolar gases along certain time courses. J. Apple. Physiol. 52(5): 1353–1357, 1982.
8. Smith, D.M., Mercer, R.R. and Eldridge, F.L., Servo control of end-tidal $CO_2$ in paralyzed animals. J. Apple. Physiol. 45(1):133–136, 1978.
9. Somers, V.K., Mark, A.L., Zavala, D.C. and Abboud, F.M. Influence of ventilation of hypocapnia on sympathetic nerve responses to hypoxia in normal humans. J. Appl. Physiol. 67(5):2095–2100, 1989.
10. Sorkness, R. And Vidruk, E. Reflex effects of isocapnic changes in ventilation of tracheal tone in awake dogs. Respir. Physiol. 69:161–172, 1987.
11. Tenney, S.M. and Reese, R.E. The ability to sustain great breathing efforts. Respir. Physiol. 5:187–201, 1968.
12. Wahba, R.W.M. and Tessler, N.J. Misleading end-tidal $CO_2$ tensions. Can. J. Anaesth. 43(8:862-6, 1996.

Table 1:
  Title: Summary of previous studies attempting to maintain constant $P_{ET}CO_2$ during hyperopia
  Legend: Method of adjustment of inspired $PCO_2$:M=manual; A=automated. Source of $CO_2$:R=rebreathing; E=external.
  $CO_2$ tensions. *Can. J. Anaesth.* 43 (8):862-6, 1996.

This requires compensating for excess ventilation by inhaling $CO_2$ either from exhaled gas or some external source. The amount of $CO_2$ required to be inhaled needs to be adjusted manually or by an automated servo-controlled mechanism, depending on how fine the control of $PaCO_2$ is required. The input signal is the $P_{ET}CO_2$. Stability of $PaCO_2$ depends on the variability of $CO_2$ production and ventilation on the one hand, and the ability of a system to compensate for this variability on the other.

The termination of the anaesthetic effects of intravenously administered drugs depends on metabolism and redistribution. The recovery time from anaesthesia is therefore determined by the drug's pharmacology and cannot be accelerated.

This is not so for inhaled anaesthetic vapours. The uptake and elimination of anaesthetic vapours is predominantly through the lungs. The partial pressure of an anaesthetic vapour in the blood going to the brain is dependent upon the equilibrium of vapour between the blood and the lungs. The concentration of vapour in the lungs in turn is dependent on the concentration of vapour in the inhaled gas, the rate of breathing, and the rate of transfer of gas between the lung and the blood. The newer anaesthetic agents desflurane and sevoflurane have very low blood solubility. Therefore the amount of drug transferred between the lungs and the blood is small and can, for discussion purposes, be ignored. Thus, for a patient waking up from a vapour anaesthetic, the greater the rate of breathing, the more vapour is eliminated from the lungs. However, in anaesthetized patients breathing spontaneously, ventilation is often depressed as a result of combined effects of residual intravenously administered anaesthetic drugs, pain relieving drugs (i.e. narcotics), the effects of surgery, as well as the respiratory depressant effect of the residual anaesthetic vapour itself.

Practically, there has been limited scope for intervention to hasten the process of eliminating vapour from the lung and thus hastening the rate of emergence from the effects of vapour anaesthesia.

Proposals in Prior Art

1. Artificial Ventilation

Manually or mechanically hyperventilating patients at the end of surgery is generally ineffective in shortening the time of recovery from anaesthesia.

a) High ventilation using the circle anaesthetic circuit results in rebreathing of exhaled gases. These gases contain anaesthetic vapour as well as $CO_2$. The $CO_2$ is eliminated by the $CO_2$ absorber in the circuit, but the exhaled anaesthetic vapour is returned to the patient.

b) The attempts at hyperventilation will result in a decrease in arterial $PCO_2$. The low arterial $PCO_2$ removes the stimulus to breathe, which in turn delays elimination of vapour (and may also prevent adequate oxygenation of the blood). This is seldom practiced.

2. Flushing the Circuit

High fresh gas flows in the circuit are inefficient in washing out the vapour from the circuits. The circle anaesthetic circuits have volumes of approximately 8 L (not counting the patient's lung volume of approximately 2.5 L). At the maximum fresh gas flows on the oxygen flow meter of 10 L/min, it would take about 4 minutes to wash out the anaesthetic vapour from the circuit alone!

3. Stimulate Breathing

In the past, some anaesthetists tried to stimulate the patient's breathing by adding $CO_2$ to the breathing circuit. The rationale was to increase the $CO_2$ concentration in the circuit, stimulate the patient to breath harder until he managed to ventilate off the $CO_2$ and some of the vapour as well. This has largely been abandoned and has been labeled a wasteful and dangerous practice.

a) It is wasteful for the reasons enumerated in 1a and 1b (vide supra). As well, the practice is wasteful in that extra $CO_2$ absorbing crystals are consumed.

b) The technique may put a patient at risk if the patient cannot respond to the extra $CO_2$ by increasing their ventilation. They will absorb it and develop a high blood $CO_2$ concentration which can be detrimental. The high $CO_2$ in the patient also causes them a good deal of distress on waking up as it makes them feel like they are not getting enough air to breathe.

4. Increase Ventilation, Keeping $PCO_2$ Constant

To increase ventilation without lowering $PCO_2$ requires adding $CO_2$ to the circuit. This can be supplied from an external source or from the subject's exhaled gas. All the presently described systems depend on a servo-controlled system, or feedback loop to regulate the amount of $CO_2$ supplied to the patient. These devices are complex, cumbersome and expensive. No such device has been reported used for hastening the elimination of anaesthetic vapour during recovery from anaesthesia.

With respect to 4 above, there are considerable limitations of servo-controlled methods, both manual or automatic. These may be discussed as follows:

1. Input Signal

Whereas the parameter that we want to keep constant is the arterial $PCO_2$, feedback systems use the $CO_2$ concentration in the expired gas, the so called end tidal $PCO_2$ ($P_{ET}CO_2$) as the input signal and endpoint. The $P_{ET}CO_2$ can be very different from the arterial $PCO_2$ in many circumstances. Furthermore, changes in $P_{ET}CO_2$ may not correlate with those in arterial $PCO_2$. This will result in $P_{ET}CO_2$ being an inappropriate input for the control of arterial $PCO_2$. For example, a smaller than usual breath decreases $P_{ET}CO_2$ (tending to increase arterial $PCO_2$), causing a servo-controller to respond with an inappropriate increase in inspired $CO_2$.

2. Gain

If, in an attempt to obtain fine control, the gain in a servo-control system is set too high, the response becomes unstable and may result in oscillation of the control variable. Conversely, if the gain is set too low, compensation lags. Over-damping of the signal results in a the response never reaching the target. To address these problems, servo-controllers require complex algorithms and expensive equipment.

3. Inherent Limitation

Servo-control systems work on the principle of detecting, and subsequently attempting to correct for, changes in $P_{ET}CO_2$. Even under ideal conditions, no such system can predict the size of an impending $V_T$ in a spontaneously breathing subject and thus deliver the appropriate $CO_2$ load.

As is apparent, people have tried to hasten the recovery of patients who have been anaesthetized and have made substantial efforts in this regard. However, they have been, for the most part, as seen above, unsuccessful. The reason for the attempts is that the benefits of faster return to consciousness, the less the need for recovery care and the less risk of nausea and post-operative respiratory complications. Thus the health care system will save substantial dollars. In this regard, the cost to the health care system of operating room and recovery area time is approximately $5.00 (Canadian Dollars) and $2.00 (Canadian Dollars) per minute respectively. The total number of anaesthetics given in North America is approximately 35,000,000/year (3.5 million and about 30 million in the United States), a conservative estimate with as high as about 50,000,000/year. The North American estimate does not include Mexico or countries in Central America. A modest average decrease in recovery time in the operating time and in the recovery room of 5 minutes each can potentially result in billions of dollars savings per year worldwide. In North America alone, the expectation of saving 5 minutes in each of the operating room and recovery area can amount to $1,000,000,000 in savings.

It is therefore an object of this invention to provide an improved breathing circuit or circuit components that can be added to a standard circle anaesthetic circuit to be used to hasten recovery of patients who have been administered vapour anaesthetics.

It is a further object of the invention to provide methods of treatment using the said circuit and the use of the said circuit during the administration of vapour anaesthetics to hasten recovery of the said patients.

Further and other objects of the invention will be realized by those skilled in the art reading the following summary of the invention and detailed description of the embodiment thereof.

SUMMARY OF THE INVENTION

According to one aspect of the invention, there is provided a new breathing circuit and components thereof that can, for example, be added to a standard circle anaesthetic circuit for hastening the recovery of patients administered vapour anaesthetics.

In accordance with the invention, the said circuit and components thereof, when combined with the general anaesthetic circle circuit cause the administration of carbon dioxide gas to the patient to maintain the same $PCO_2$ in the patient independent of the rate of ventilation (so long as the said rate of ventilation is greater than a control rate of ventilation) but permit the rate of anaesthetic vapour elimination from the lungs of the patient to vary directly as the total ventilation by the patient, whether the patient is breathing normally or is hyperventilating. Thus, the vapour anaesthetic is eliminated from the lungs. However, the carbon dioxide is not eliminated from the lungs at a rate greater than the resting rate of the patient or a predetermined control rate. (The predetermined rate of elimination of $CO_2$ may be set based on the rate of administration of the fresh gas into the circuit as discussed below.)

Thus, according to another aspect of the invention, the simple breathing circuit comprises components which together form the simple circuit and comprise (a) an exit port from which the gases exit from the circuit to the patient, (b) a non-breathing valve which constitutes a one-way valve permitting gases to be delivered to the exit port to be delivered to the patient but which non-breathing valve when the patient breathes into the exit port does not permit the gases to pass the non-rebreathing valve into the portion of the circuit from which the gases are delivered but passes them to ambient or elsewhere, (c) a source of gas (which may be oxygen or air or other gases but does not contain $CO_2$) (air contains physiologically insignificant amounts of $CO_2$) in communication with the non-breathing valve to be delivered through the valve to the patient, (d) a fresh gas reservoir in communication with the source of fresh gas flow for receiving excess gas not breathed by the patient from the source of gas and for storing same and when the patient breathes and withdraws amounts of gas from the source of gas flow also enables the patient to receive gas from the fresh gas reservoir in which the gases have been stored, (e) a reserve gas supply containing $CO_2$ and other gases (usually oxygen) wherein the partial pressure of the $CO_2$ is approximately equal to the partial pressure of the $CO_2$ in the patient's mixed venous blood, for being delivered to the non-rebreathing valve as required by the patient to make up that amount of gas required by the patient when breathing that is not fulfilled from the gases delivered from the source of gas flow and fresh gas reservoir, the said source of gas and fresh gas reservoir and reserve gas supply being disposed on the side of the valve remote from the exit port.

Preferably a pressure relief valve is in communication with the fresh gas reservoir, in the event that the fresh gas reservoir overfills with gas so that the fresh gas reservoir does not break, rupture or become damaged in any way.

The reserve gas supply preferably includes a demand valve regulator so that where the additional gas is required, the demand valve regulator opens the communication of the reserve gas supply to the non-rebreathing valve for delivery of the gas to the non-rebreathing valve and where not required the demand valve regulator is closed and only fresh gas flows from the source of fresh gas and from the fresh gas reservoir to the non-rebreathing valve. The source of fresh gas is set to supply fresh gas (non-$CO_2$-containing gas) at a rate equal to the desired alveolar ventilation for the elimination of $CO_2$.

The basic concept underlying my approach is that when breathing increases, the rate of flow of fresh gas (inspired $PCO_2$=0) from the fresh gas flow contributing to elimination of $CO_2$ is kept constant. The remainder of the gas inhaled by the subject (from the reserve gas supply) has a $PCO_2$ equal to that of mixed venous blood, does not contribute to a $CO_2$ concentration gradient between mixed venous blood and alveolar gas, and thus does not contribute to elimination of $CO_2$. If there is access to mixed venous blood (such as if a catheter is present in the pulmonary artery, the mixed venous $PCO_2$ can be measured directly. If there is no possibility of measuring, then an estimation can be made from $P_{ET}CO_2$. $P_{ET}CO_2$ is determined by measuring the $PCO_2$ of expired using a capnograph usually present or easily available in an operating facility by persons skilled in the art.

In effect, the device passively, precisely and continuously matches the amount of $CO_2$ breathed in by the patient to the amount of total breathing, thereby preventing any perturbation of the arterial $PCO_2$. This is opposed to servo-controllers which are always attempting to compensate for changes. Persons skilled in the art, however, may automate the circuit by using a servo-controller or computer to monitor and deliver the amounts from the reserve gas supply.

According to another aspect of the invention, the new simple breathing circuit is used to treat a patient to enable the patient to recover more quickly from, and to hasten the recovery of the patient after, vapour anaesthetic administration.

According to another aspect of the invention, the use of the said circuit is made in the manufacture of a device to hasten the recovery of patients from administration of vapour anaesthetics.

According to another aspect of the invention, the use of said circuit is made to hasten the recovery of patients from vapour anaesthetics administration.

According to another aspect of the invention, a method of treatment of an animal (for example, a person) is provided (such as to enable such animal to recover from vapour anaesthetics administration), the method comprising delivering to a patient gases which do not contain $CO_2$ at a specified rate, and gases containing $CO_2$ to maintain the same $PCO_2$ in the animal independent of the rate of ventilation, at a rate of ventilation of the animal which exceeds the rate of administration of the gases which do not contain $CO_2$.

Therefore, when the rate of ventilation of the animal exceeds the rate of delivery to the animal of non-$CO_2$-containing gases inhaled by the animal, the $CO_2$-containing gases inhaled by the animal maintain the $PCO_2$ in the animal constant.

Thus, with respect to the use of the invention to eliminate anaesthetic vapour from the lungs, the total ventilation of combined gases which includes the $CO_2$-containing, and non-$CO_2$ containing, gases act to eliminate vapour from the lungs.

This circuit and methods of treatment can also be used for any circumstance where one wants to dissociate the minute ventilation from elimination of carbon dioxide such as respiratory muscle training, investigation of the role of pulmonary stretch receptors, tracheobronchial tone, expand the lung to prevent atelectasis, and control of respiration and other uses as would be understood by those skilled in the art.

The circuit and methods of treatment may also be used by deep sea divers and astronauts to eliminate nitrogen from the body. It can also be used to treat carbon monoxide poisoning under normal baric or hyper baric conditions. The fresh gas will contain 100% oxygen, and the reserve gas will contain approximately 6% $CO_2$ and approximately 94% oxygen. Neither the fresh gas nor the reserve gas supply will, in this case, contain nitrogen.

BRIEF DESCRIPTION OF THE DRAWINGS

(FIG. 3 shows the modifications made specifically to the structure of FIG. 1 to combine it with the structure in FIG. 2 which is now shown in FIG. 4A.)

DETAILED DESCRIPTION OF EMBODIMENTS

Figure 1:
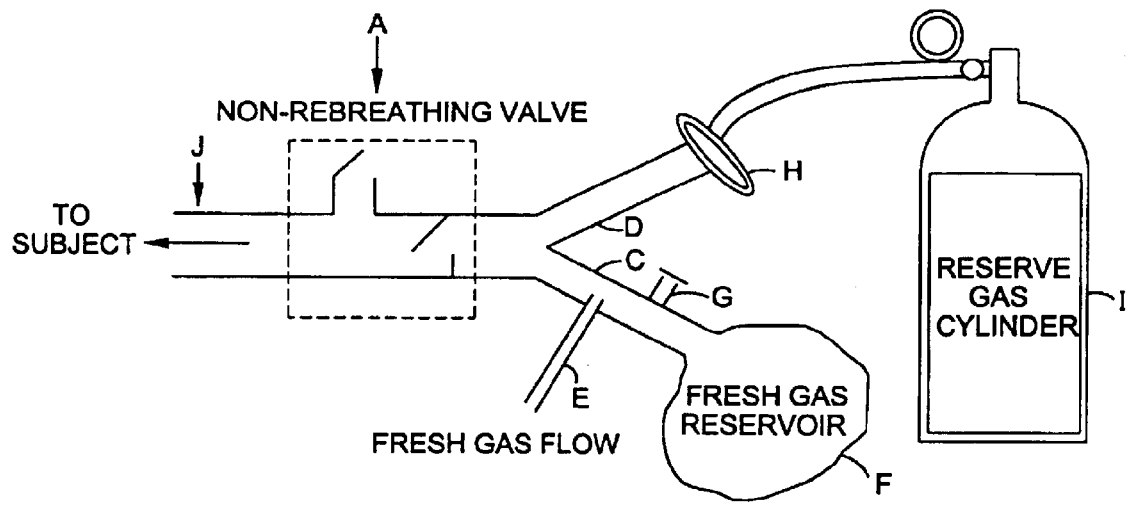
FIG. 1 illustrates schematically the nature of the simple breathing circuit and components which enable the patient to recover more quickly from vapour anaesthetics administration. The said device shown enables the $PCO_2$ to remain constant despite increase in minute ventilation which thereby permits faster elimination of the vapour anaesthetics.

The circuit (FIG. 1) consists of a non-rebreathing valve (A) connected distally to two ports (C and D). The first port is connected in parallel to a source of fresh gas (E) (which does not contain $CO_2$) and a fresh gas reservoir (F). A one-way pressure relief valve (G) prevents overfilling of the reservoir (F) by venting excess fresh gas. The second port (D) is connected via a one-way valve (H), to a source of gas (containing $CO_2$) whose $PCO_2$ is equal approximately to that of the mixed venous $PCO_2$. We call this the "reserve gas" (I). Non-rebreathing valve A is connected to exit port J (from which the patient breathes).

Functional Analysis of Circuit Maintaining Constant $PCO_2$ with Hyperventilation When the minute ventilation "V" is less than or equal to the fresh gas flow "FGF" from (E), the subject inhales only fresh gas (non-$CO_2$-containing gas). When V exceeds FGF, the reservoir (F) containing fresh non-$CO_2$-containing gas empties first and the balance of inhaled gas is drawn from the reserve gas (I) which contains $CO_2$. The reserve gas is considered not to participate in $CO_2$ exchange ensuring that the actual ventilation provided is limited by FGF. If the rate of FGF is 5 L/minute and the patient breathes at 5 L/minute or less, then the patient will inhale only non-$CO_2$-containing gas that comes from fresh gas flow sources (E and F). If minute ventilation exceed FGF, the difference between minute ventilation and fresh gas flow is made up from gas from reserve gas (I) which contains $CO_2$ at a concentration that does not provide a gradient for elimination of $CO_2$ in the patient.

Figure 2:
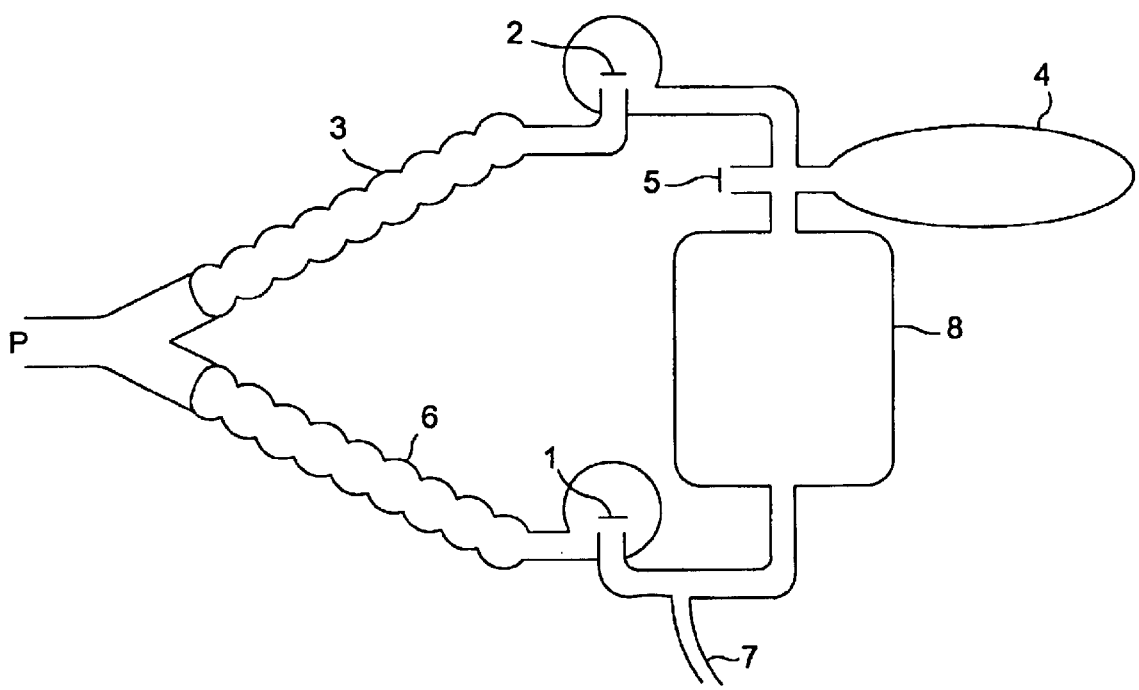
FIG. 2 illustrates schematically portions of a standard circle anaesthetic circuit generally known to persons skilled in the art.

Application of Circuit to Anaesthesia Circle Circuit
The Schematic of the Standard Anaesthetic Circle Circuit, Spontaneous Ventilation (FIG. 2)

When the patient exhales, the inspiratory valve (1) closes, the expiratory valve (2) opens and gas flows through the corrugated tubing making up the expiratory limb of the circuit (3) into the rebreathing bag (4). When the rebreathing bag is full, the airway pressure-limiting (APL) valve (5) opens and the balance of expired gas exits through the APL valve into a gas scavenger (not shown). When the patient inhales, the negative pressure in the circuit closes the expiratory valve (2), opens the inspiratory valve (1), and directs gas to flow through the corrugated tube making up the inspiratory limb of the circuit (6). Inspiration draws all of the gas from the fresh gas hose (7) and makes up the balance of the volume of the breath by drawing gas from the rebreathing bag (4). The gas from the rebreathing bag contains expired gas with $CO_2$ in it. This $CO_2$ is extracted as the gas passes through the $CO_2$ absorber (8) and thus is delivered to the patient (P) without $CO_2$, (but still containing exhaled anaesthetic vapour, if any).

Figure 3:
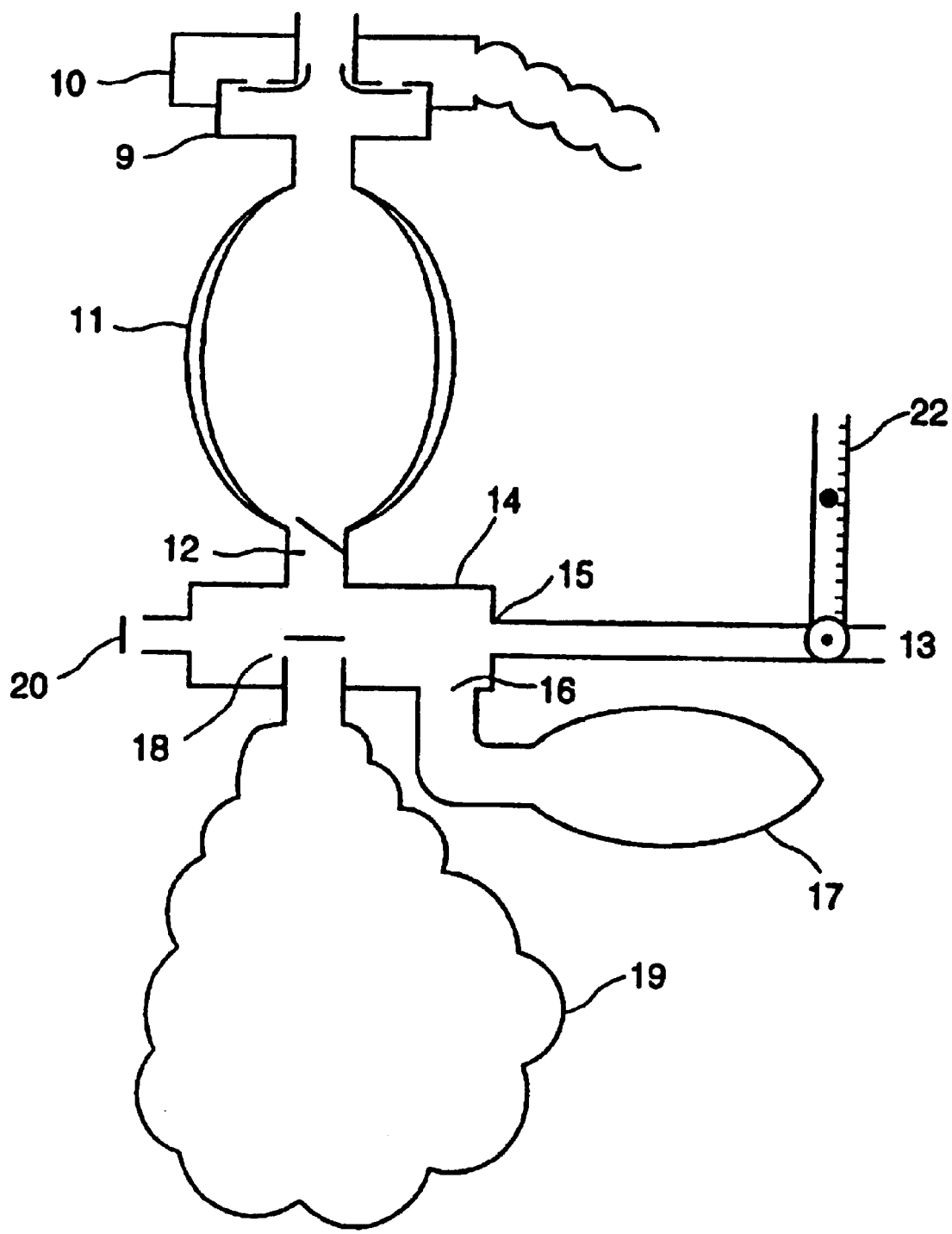
FIG. 3 illustrates schematically the simple breathing circuit in one embodiment added to the portions of the circle anaesthetic circuit shown schematically in FIG. 2, illustrating modifications of the circuit shown schematically in FIG. 1 for use with the generally known circuit shown in FIG. 2. (It would be clear to persons skilled in the art that depending upon the circuit used as the circle anaesthetic circuit, different modifications on the basic circuit shown in FIG. 1 will be made).

Modification of the Circuit (FIG. 3) to Allow Hyperventilation of Patients Under Anaesthesia The modified circuit consists of
1. a circuit which acts functionally like a standard self inflating bag (such as made by Laerdal) consisting of
   a) a non rebreathing valve, such as valve #560200 made by Laerdal, that functions during spontaneous breathing as well as manually assisted breathing (9);
   b) an expired gas manifold, such as the Expiratory Deviator #850500, to collect expired gas (10) and direct it to a gas scavenger system (not shown) or to the expiratory limb of the anaesthetic circuit (FIG. 4);
   c) a self inflating bag (11) whose entrance is guarded by a one way valve directing gas into the self inflating bag (12).
2. a source of fresh gas, (i.e. not containing vapor) e.g. oxygen or oxygen plus nitrous oxide (13) with a flow meter (22).
3. a manifold (14) with 4 ports:
   a) a port (15) for input of fresh gas (13);
   b) a port (16) for a fresh gas reservoir bag (17);
   c) a port to which is attached a one way inflow valve that opens when the pressure inside the manifold is 5 cm $H_2O$ less than atmospheric pressure, such as Livingston Health Care Services catalog part #9005, (18) (assuring that all of the fresh gas is utilized before opening);
   d) a bag of gas (19) whose $PCO_2$ is equal approximately to that of the mixed venous $PCO_2$ connected to inflow valve (18) (Alternatively, the valve and gas reservoir bag can be replaced by a demand regulator, such as Lifetronix MX91120012, similar to that used in SCUBA diving, and a cylinder of compressed gas);
   e) a port to which is attached a one way outflow valve (20), such as Livingston Health Care Services catalog part #9005, that allows release of gas from the manifold to atmosphere when the pressure in the manifold is greater than 5 cm $H_2O$.

Figure 4A:
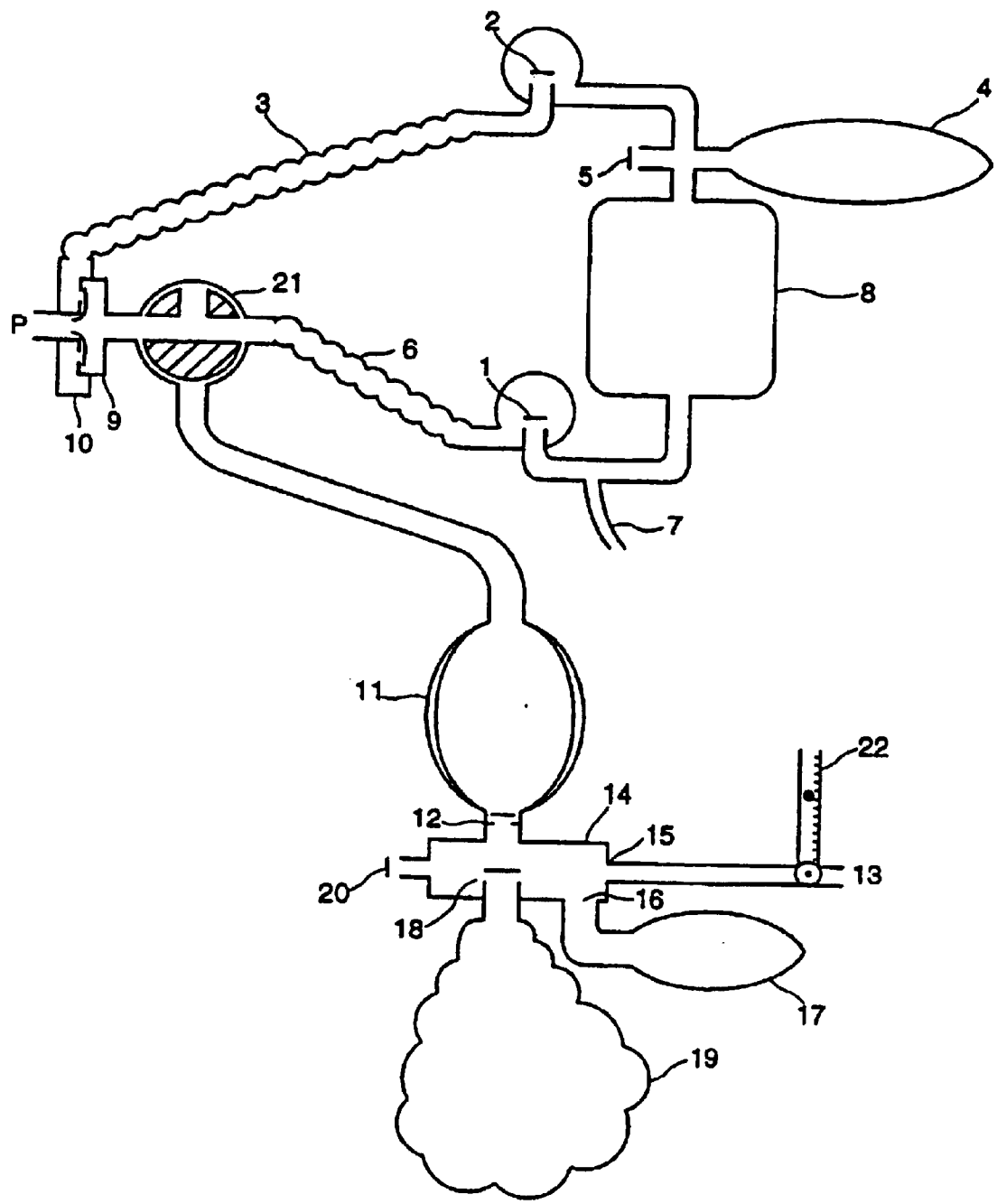
FIG. 4A illustrates the structure shown in FIG. 3, now combined with the general structure shown in FIG. 2.
Figure 4B:
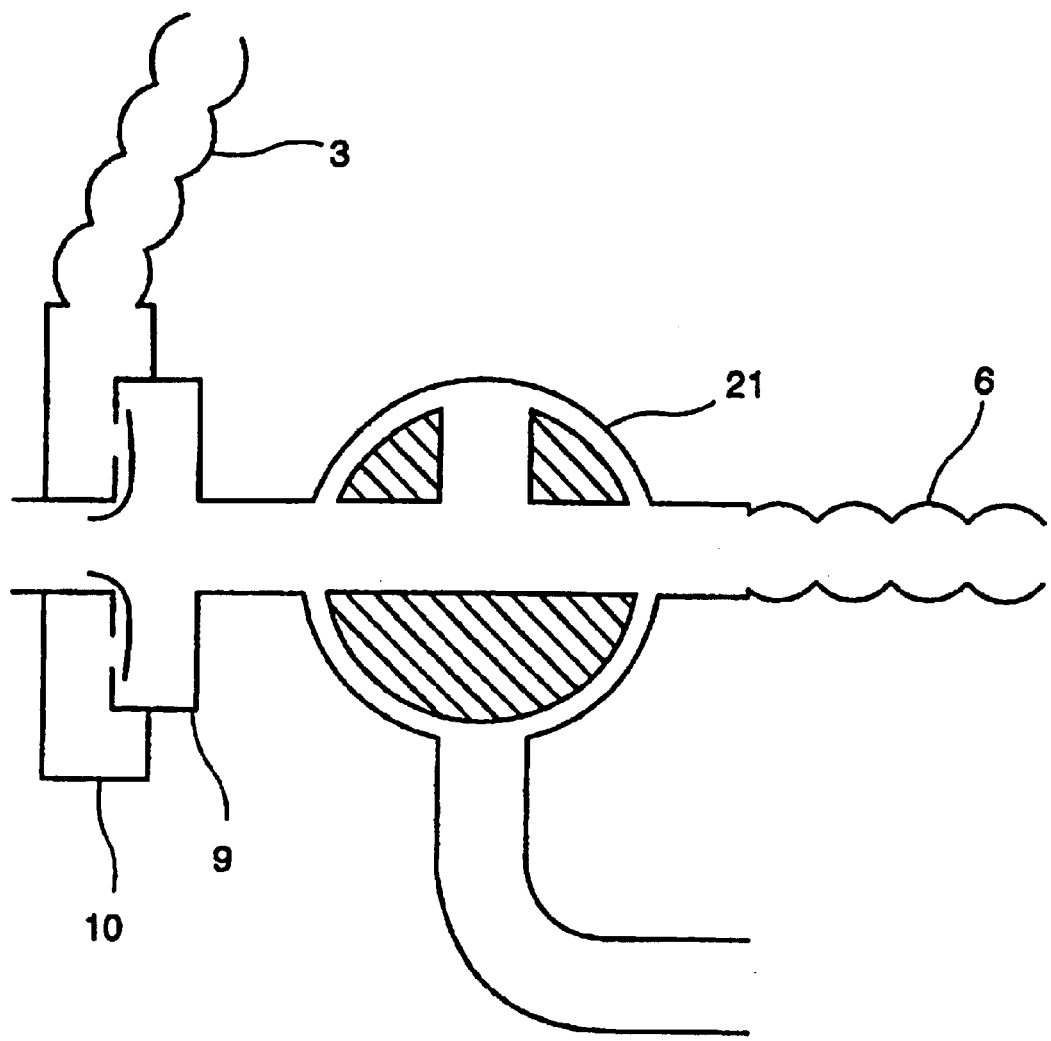
FIGS. 4B and 4C illustrate schematically close up portions of one portion of the structure shown in FIG. 4A in different positions.

Method of Operation in an Anaesthetic Circuit (FIG. 4A)

The distal end of the nonrebreathing valve (Laerdal type) (9), is attached to the patient.

Figure 4C:
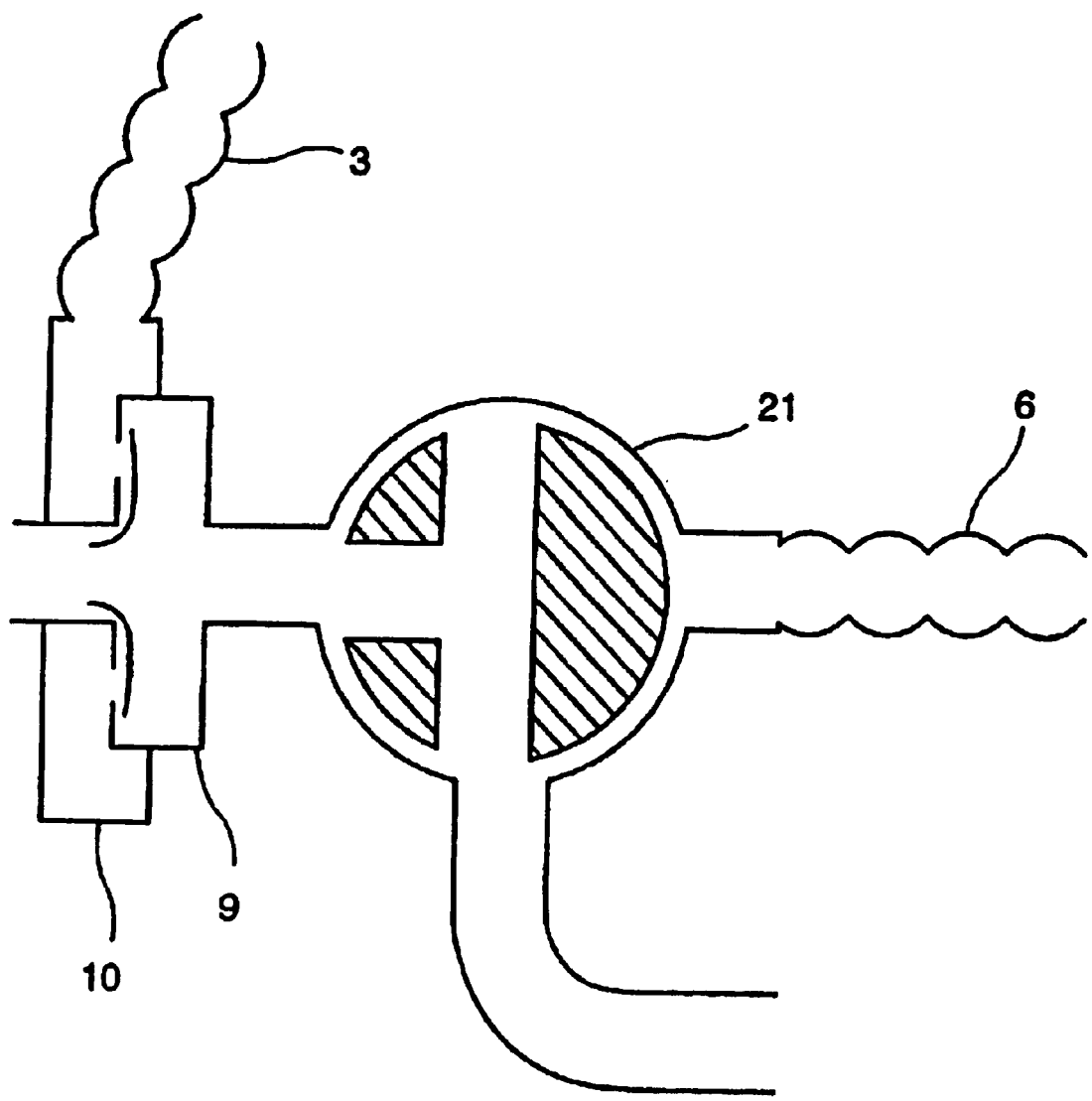

The proximal port of the nonrebreathing valve is attached to a 3 way respiratory valve (21) which can direct inspiratory gas either from the circle anaesthetic circuit (FIG. 4B) or from the new circuit (FIG. 4C). The expiratory manifold (10) of the self inflating bag's non rebreathing valve is attached to the expiratory limb of the anaesthetic circuit (3). Regardless of the source of inspired gas, exhalation is directed into the expiratory limb of the anaesthetic circuit.

To maximize the elimination of anaesthetic vapour from the patient's lungs, the 3-way respiratory stopcock is turned such that patient inspiration is from the new circuit (FIG. 4C). Thus inspired gas from the very first breath after turning the 3-way valve onward contains no vapour, providing the maximum gradient for anaesthetic vapour elimination.

An increased breathing rate will further enhance the elimination of vapour from the lung. If breathing spontaneously, the patient can be stimulated to increase his minute ventilation by lowering the FGF (22) thereby allowing the $PCO_2$ to rise. Using this approach the $PCO_2$ will rise and plateau independent of the rate of breathing, resulting in a constant breathing stimulus. All of the ventilation is effective in eliminating vapour.

If the patient is undergoing controlled ventilation, he can also be hyperventilated with the self inflating bag (11). In either case, the patient's $PCO_2$ will be determined by the FGF (22). As long as the FGF remains constant the $PCO_2$ will remain constant independent of the minute ventilation.

To illustrate the effectiveness of the circuit we performed a number of tests with respect to humans and dogs. The humans were breathing spontaneously and the dogs were mechanically ventilated.

Human Subjects

After obtaining institutional ethics board approval and informed consent, four healthy subjects aged 19–25 y breathed through the circuit by means of a mouth piece while wearing nose clips. During normal breathing, the FGF was set equal to V by adjusting the FGF such that the bag containing fresh gas just emptied at the end of each inhalation. Subjects were then instructed to breathe maximally ("breathe as hard as you can") for 3 min. Flows were recorded by means of a Pitot tube (Voltek Enterprises, Willowdale Canada) and the signal integrated to obtain volume. $CO_2$ was sampled continuously at the mouthpiece (Medical Gas Analyzer LB-2, Sensormedics Corp., Anaheim, Calif.). Analog signals were digitized at 60 samples·$S^{-1}$ and recorded using data acquisition software (WINDAQ/200, DATAQ instruments, Inc. Akron Ohio).

Studies in Dogs

Following institutional ethics board approval, 6 mongrel dogs of either sex weighing 20–25 kg were anaesthetized with methohexital (5–7 mg·$kg^{-1}$ for induction followed by 150–300 mg·$kg^{-1}$·$min^{-1}$) and intubated. Adequacy of anaesthetic depth was deduced from the eye lash reflex, lack of spontaneous movements, and stable heart rate and blood pressure. A catheter was placed in the femoral artery for monitoring blood pressure and periodic sampling of blood for gas analysis. The dogs were ventilated with a conventional mechanical piston ventilator (Harvard Apparatus model 618, South Natick, Mass.). For each dog, an inflation volume (VT) of 400 ml and a frequency (f) of 10 $min^{-1}$ (duty cycle, 0.5) were used. All dogs were ventilated to just below their apneic thresholds (by increasing VT about 50 mL) so that they made no respiratory efforts. Tidal $CO_2$ was sampled continuously (Ametek, Thermox Instruments Division, Pittsburgh, Pa.) at the proximal end of the endotracheal tube. Flow was measured with a pneumotachograph (Vertek series 47303A, Hewlett-Packard) and the signal integrated to obtain volume. Analog signals were digitized at 17 samples·$S^{-1}$ and recorded using the same data acquisition software as that used in studies on human subjects.

Because of differences in initial $PaCO_2$s among dogs (reflecting individual sensitivities to $CO_2$, differences in anaesthetic levels, or differences in VT/body weight ratio), the $CO_2$ concentration in the reserve gas was arbitrarily adjusted for each dog to 1.5 ±0.5% above its $FetCo_2$ to approximate the mixed venous $PCO_2$ ($PvCO_2$) (see Table II). To allow greater flexibility in setting the concentration of $CO_2$ in the reserve gas, the circuit was modified by replacing the demand valve with a one-way PEEP (positive end expiratory pressure) valve and the cylinder with a bag containing premixed gas. This circuit is functionally identical to that used in studies on humans. The circuit was connected to the intake port of the ventilator. Under control conditions, FGF was adjusted so that the fresh gas reservoir just emptied during each ventilator cycle; this end point was confirmed by a slight rise in $FICO_2$ above zero. After a steady-state had been reached (difference <1.5 mm Hg in two successive $PaCO_2$'s taken 5 minutes apart), $V_T$ was increased at 5 minute intervals from 400 to 600 to 900 to 1200 mL. In a second trial at a fixed $V_T$ (approximately 400 mL) and fixed FGF, f was increased at 5 minute intervals from 10 to 14 to 18 to 22 $min^{-1}$. A blood sample for the determination of blood gases was drawn from the femoral artery at the beginning and end of each 5 min interval.

All data are expressed as means ± standard deviation. We tested for significant differences using one- or two-way ANOVA with post hoc analysis where appropriate. A p value less than 0.05 was considered significant.

Results

Human Subjects

Figure 5:
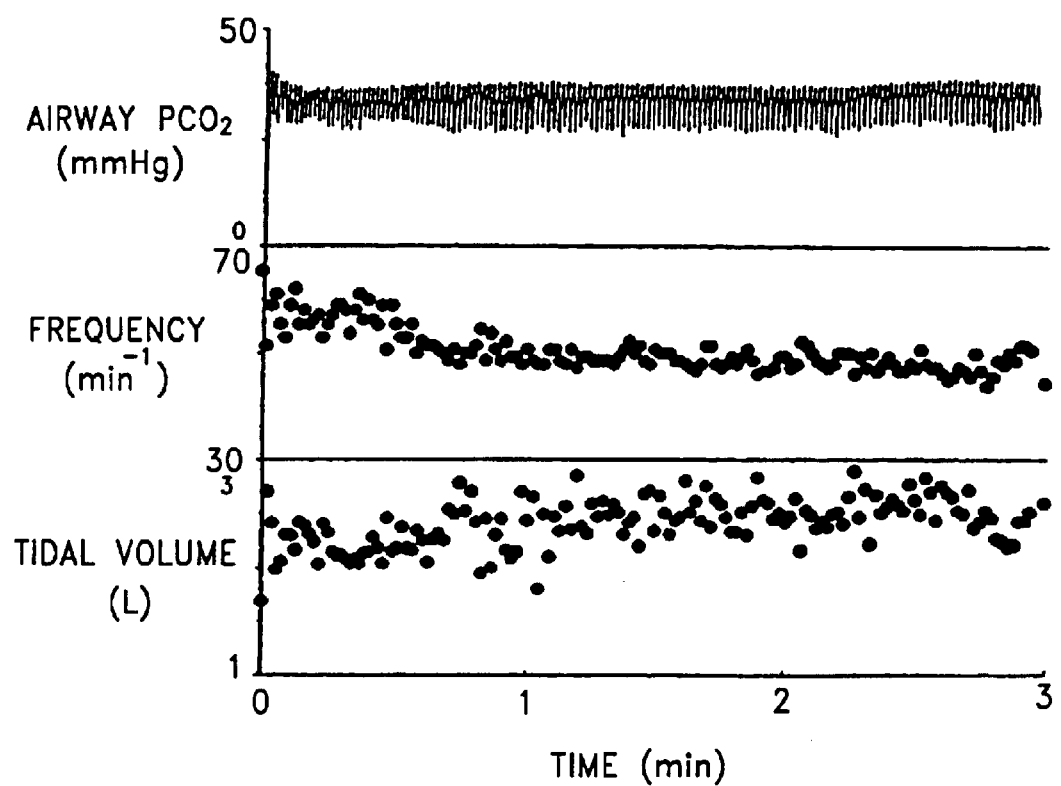
FIG. 5 graphs the $V_T$ (Tidal Volume) and $P_{ET}CO_2$.

FIG. 5 presents the $V_T$ and $P_{ET}CO_2$ of subject 1 during 3 min of maximal ventilatory effort. Results for all subjects are summarized in Table III; data represent average values for 10 breaths at 0 (the onset of hyperventilation), 1.5 and 3 min. $P_{ET}CO_2$ did not change significantly from control values throughout the course of hyperventilation (p=0.08, ANOVA). There was considerable variability in V and breathing patterns between subjects but individual subjects tended to sustain a particular breathing pattern throughout the run.

Dogs

Figure 6:
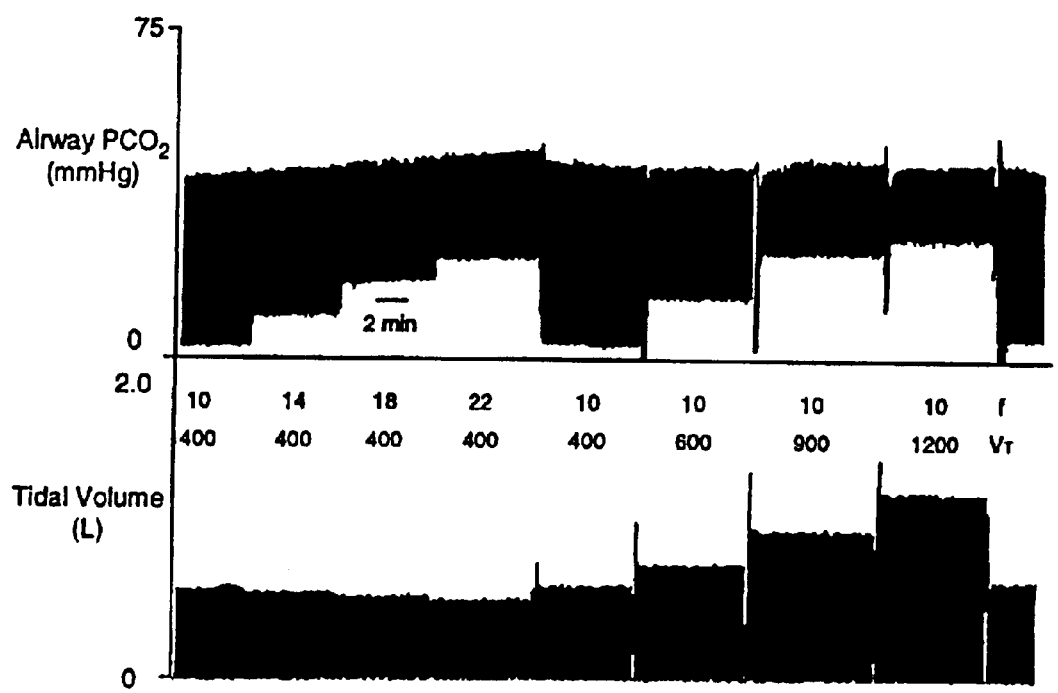
FIG. 6 graphs traces of airway $PCO_2$ and $V_T$.
Figure 7A:
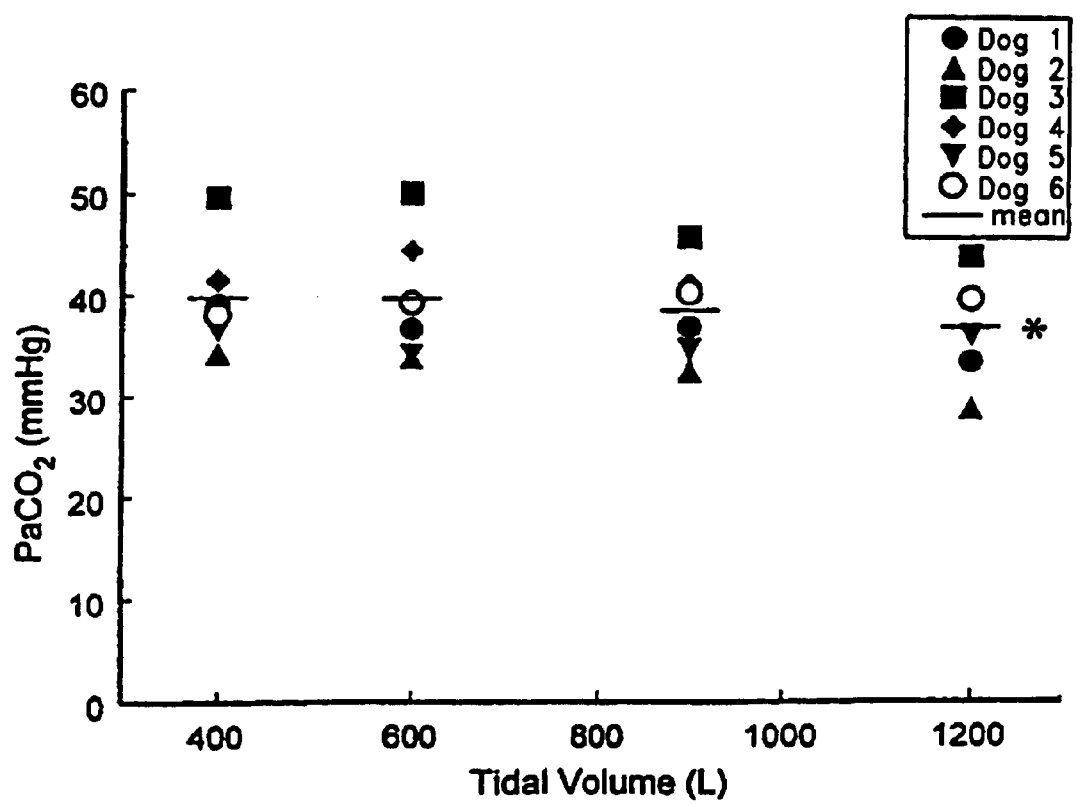
FIGS. 7A, 7B and 8A and 8B graphically depict changes in $PaCO_2$ and $P_{ET}CO_2$.
Figure 7B:
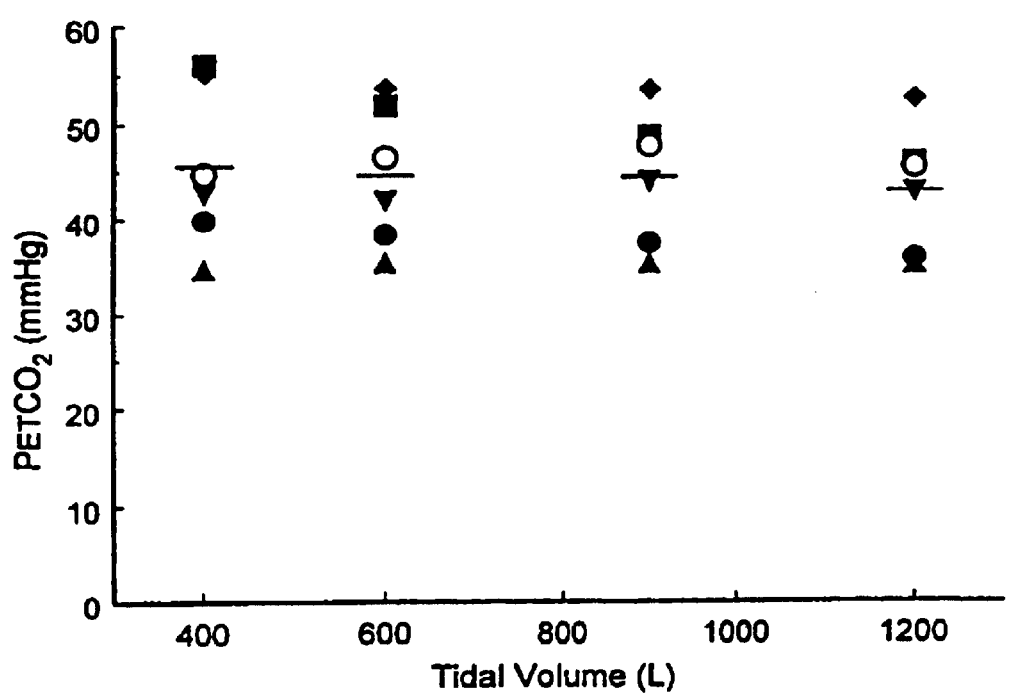
Figure 8A:
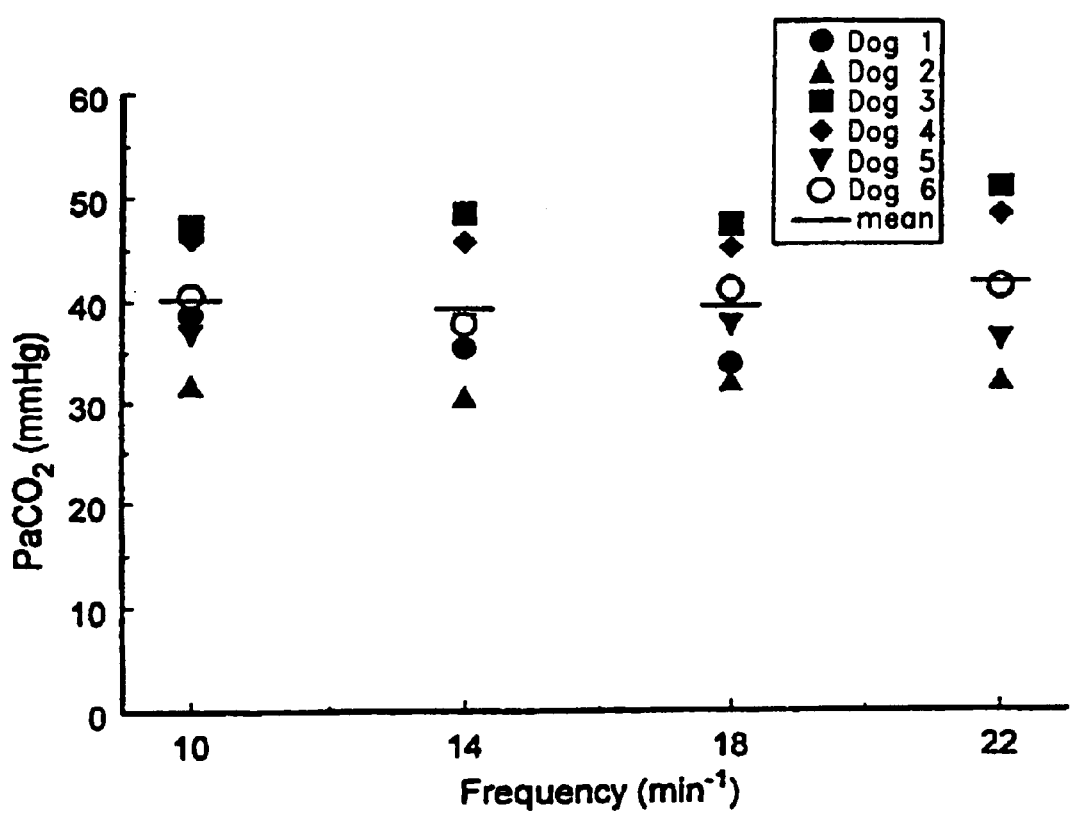
Figure 8B:
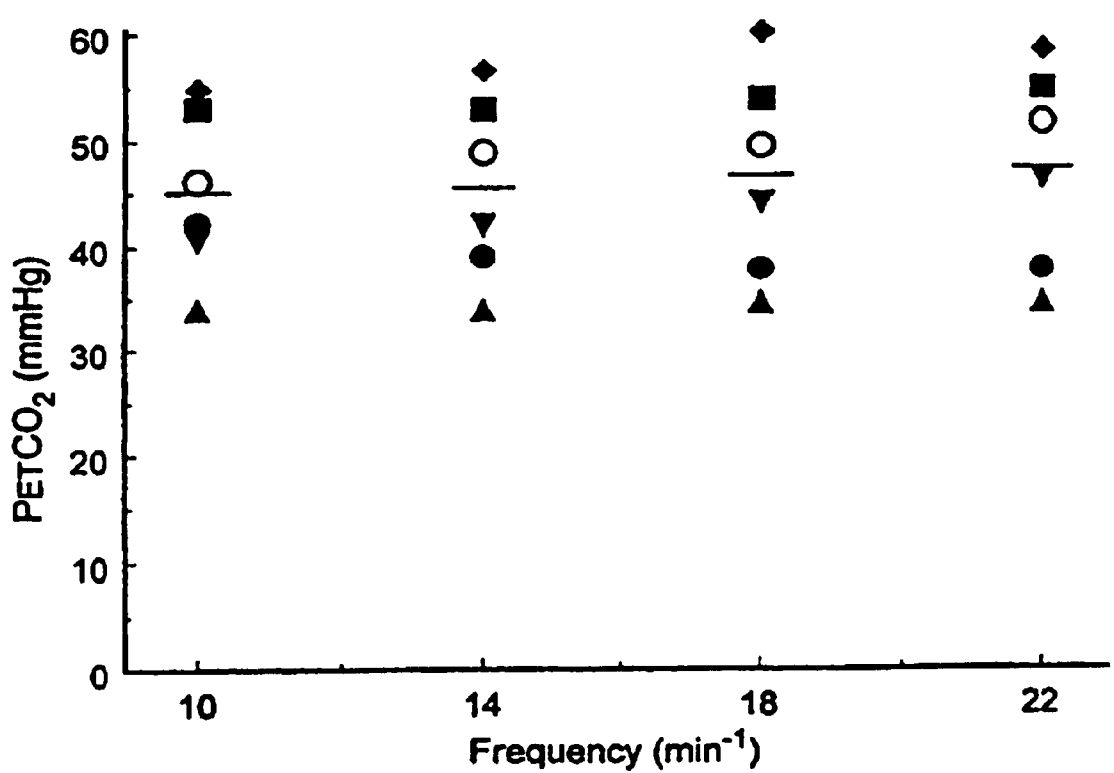

FIG. 6 presents traces of airway $PCO_2$ and $V_T$ for dog #5 during changes in f or $V_T$. FIGS. 7 and 8 show the changes in $PaCO_2$ and the $P_{ET}CO_2$ in all dogs during changes in for $V_T$. Increases in f did not significantly affect mean $PaCO_2$ or $P_{ET}CO_2$ (p=0.28 and p=0.11, respectively; ANOVA). Increases in $V_T$ decreased mean $PaCO_2$ from control only at $V_T$ Of 1200 mL (p=0.01); in contrast, changes in $V_T$ did not affect mean $P_{ET}CO_2$ (p=0.25). The mean absolute change in $PaCO_2$ between control and the highest ventilation was 2.2±1.8 mmHG (range 0.4 to 4.8) for f and 3.4±2.3 mmHG (range 0.4 to 4.8) for f and 3.4±2.3 mmHG (range 0.4 to 5.6) for $V_T$.

Commentary

The system minimized decreases in $P_{ET}CO_2$ over a wide range of ventilation (56 to 131 L $min^{-1}$) and breathing patterns, in hyperventilating human subjects and in mechanically hyperventilated dogs (4 to 12 L $min^{-1}$). The variability in $PaCO_2$ in the hyperventilated dogs, although small, may have been due to a) imprecise matching of reserve gas $PCO_2$ to the dog's $PvCO_2$s;b) prolonged duration of the maneuver in dogs (>15 min versus 3 min for human subjects) and c) the extent of hyperventilation (see below). In addition, the different levels of ventilation may have induced changes in systemic and pulmonary blood flow (ventilation-perfusion matching, physiological and anatomical dead space), thereby affecting $PaCO_2$ and $PvCO_2$. Despite these sources of variability, the range over which $PaCO_2$ varied in my studies in dogs was similar to those reported in studies utilizing more complex equipment (see Table 1).

Conventional servo-controlled techniques designed to prevent changes in $PCO_2$ with hyperpnea are less affected by changes in $CO_2$ production than the circuit; however, they have other limitations. The assumption that detected changes in $P_{ET}CO_2$ are due to a change in $PaCO_2$ is not always warranted (14). Small changes in ventilatory pattern can 'uncouple' $P_{ET}CO_2$ from $PaCO_2$, resulting in $P_{ET}CO_2$ being an inappropriate input for the control of $PaCO_2$. For example, a smaller $V_T$ decreases $V_A$ (which tends to increase $PaCO_2$) but will also decrease $P_{ET}CO_2$, causing a servo-controller to respond with an inappropriate increase in inspired $CO_2$. Even under ideal conditions, a servo-controlled system attempting to correct for changes in $P_{ET}CO_2$ cannot predict the size of an impeding $V_T$ in a spontaneously breathing subject and thus deliver the appropriate $CO_2$ load. If in an attempt to obtain fine control the gain in a servo-control system is set too high, the response becomes unstable and may result in oscillation of the control variable (11). Conversely, if the gain is set too low, compensation lags (9). Over-damping of the signal results in a response never reaching the target. To address these problems, servo-controllers require complex algorithms (16) and expensive equipment.

When $CO_2$ production is constant, the circuit has the theoretical advantage over servo-controlled systems in that it provides passive compensation for changes in V. This minimizes changes in $V_A$, pre-empting the need for subsequent compensation. Maintenance of a nearly constant $V_A$ occurs even during irregular breathing, including brief periods when V is less than the FGF. Under this circumstance, excess FGF is stored in the fresh gas reservoir and subsequently contributes to $V_A$ when ventilation exceeds FGF.

When $CO_2$ production increases during hyperventilation, as would occur with increased work of breathing or exercise, my method requires modification. To compensate, additional $V_A$ can be provided either by increasing FGF or by lowering the $PCO_2$ of the reserve gas below the $PvCO_2$, as expressed in the following equation:

$$V_A = FGF + (V - FGF)(PvCO_2 - \text{reserve gas } PCO_2)$$

Because spontaneously breathing subjects had such variable V during hyperventilation, compensating for the $CO_2$ production by modifying FGF would have required constant adjustment. We therefore chose to decrease the $PCO_2$ of the reserve as to establish a concentration gradient between the $PCO_2$ of the reserve gas and the $PvCO_2$; when this is constant, $V_A$ is a function of V. We found that, over the wide range of V exhibited by the subjects, a concentration of 5.5% $CO_2$ in the reserve gas (instead of 6.5% which corresponds to a $PvCO_2$ of 46 mmHG) provided the optimal gradient to compensate for increases in $CO_2$ production resulting from increased work of breathing.

I therefore have described a simple circuit that disassociates $V_A$ from V. It passively minimizes increases in $V_A$ that would normally accompany hyperventilation when $CO_2$ production is constant. It can be modified to compensate for increases in $CO_2$ production. The circuit may form the basis for a simple and inexpensive alternative to servo-controlled systems for research and may have therapeutic applications.

TABLE II

| Dog # | Weight (kg) | Initial FETCO$_2$ (%) | Bag FCO$_2$ (%) |
|---|---|---|---|
| 1 | 22 | 5.3 | 7.0 |
| 2 | 20 | 4.6 | 6.6 |
| 3 | 20 | 7.1 | 9.0 |
| 4 | 24 | 7.3 | 9.0 |
| 5 | 25 | 5.5 | 6.9 |
| 6 | 20 | 6.0 | 7.2 |

TABLE III

| | | Time | | |
|---|---|---|---|---|
| Subject # | Control | 0 | 1.5 | 3 |
| End Tidal PCO$_2$ (mmHg) | | | | |
| 1 | 40.3 | 33.6 | 34.9 | 35.6 |
| 2 | 36.6 | 30.9 | 28.1 | 28.0 |
| 3 | 42.0 | 42.5 | 43.2 | 42.7 |
| 4 | 41.0 | 34.5 | 38.8 | 38.8 |
| Frequency (min$^{-1}$) | | | | |
| 1 | | 57 | 50 | 47 |
| 2 | | 89 | 87 | 88 |
| 3 | | 31 | 30 | 30 |
| 4 | | 149 | 130 | 127 |
| Tidal Volume | | | | |
| 1 | | 2.30 | 2.49 | 2.58 |
| 2 | | 0.85 | 0.72 | 0.63 |
| 3 | | 2.60 | 2.64 | 2.26 |
| 4 | | 0.78 | 0.62 | 0.60 |
| Minute Ventilation (L · min$^{-1}$) | | | | |
| 1 | | 131 | 124 | 118 |
| 2 | | 75 | 63 | 56 |
| 3 | | 80 | 78 | 68 |
| 4 | | 117 | 80 | 76 |

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

What is claimed:

1. A breathing circuit system for ventilating an anesthetized patient, the system comprising:

(a) a standard primary circle anaesthetic circuit comprising a one-way inspiratory limb for delivering re-breathed gas and a one-way expiratory limb for accepting expired gas;

(b) a supplementary respiratory circuit for supplying non-rebreathed gas and comprising a source of non-rebreathed substantially carbon dioxide-free gas, a non-rebreathed fresh gas reservoir for storing fresh gas, a source of non-rebreathed reserve gas containing carbon dioxide whose PCO$_2$ value is selectable, and a gas delivery conduit;

(c) a non-rebreathing valve disposed in communication with the inspiratory limb; and (d) a respiratory valve disposed in communication with both the inspiratory limb and the delivery conduit for selectively permitting passage of gas from the inspiratory limb or from the delivery conduit.

* * * * *